United States Patent [19]

Thominet et al.

[11] 4,364,867

[45] Dec. 21, 1982

[54] N-(1-METHYL-2-PYRROLIDINYLMETHYL)-2,3-DIMETHOXY-5-METHYLSULFAMOYL BENZAMIDE AND ITS DERIVATIVES

[75] Inventors: Michel Thominet; Jacques Perrot, both of Paris, France

[73] Assignee: Societe d'Etudes Scientifiques et Industrielles de l'Ile de France, Paris, France

[21] Appl. No.: 215,210

[22] Filed: Dec. 11, 1980

Related U.S. Application Data

[63] Continuation of Ser. No. 82,421, Oct. 5, 1979, Pat. No. 4,263,316.

[30] Foreign Application Priority Data

Oct. 11, 1978 [FR] France ............................. 78 29005

[51] Int. Cl.³ .......................................... C07D 207/09
[52] U.S. Cl. ....................................... 548/567; 560/12
[58] Field of Search ................................... 260/326.47

[56] References Cited

U.S. PATENT DOCUMENTS

| | | | |
|---|---|---|---|
| 3,342,826 | 9/1967 | Miller et al. | 424/274 |
| 3,862,139 | 1/1975 | Podesva et al. | 260/326.47 |
| 3,891,671 | 6/1975 | Thominet | 260/326.47 |
| 4,029,673 | 6/1977 | Bulteau | 260/326.47 |
| 4,158,060 | 6/1979 | Kaplan et al. | 424/274 |

*Primary Examiner*—Alton D. Rollins
*Attorney, Agent, or Firm*—Fitzpatrick, Cella, Harper & Scinto

[57] ABSTRACT

The present invention relates to a novel veratramide, N-(1-methyl-2-pyrrolidinyl-methyl)-2,3-dimethoxy-5-methylsulphamoyl benzamide, its pharmacologically acceptable acid addition salts, its quaternary ammonium salts, its oxides and its levorotatory and dextrorotatory isomers and their use in the treatment of disorders of the lower urinary apparatus.

1 Claim, No Drawings

N-(1-METHYL-2-PYRROLIDINYLMETHYL)-2,3-DIMETHOXY-5-METHYLSULFAMOYL BENZAMIDE AND ITS DERIVATIVES

This application is a continuation of application Ser. No. 082,421, filed Oct. 5, 1979, now U.S. Pat. No. 4,263,316.

The present invention relates to a novel veratramide, N-(1-methyl-2-pyrrolidinyl-methyl)-2,3-dimethoxy-5-methylsulphamoyl benzamide, its pharmacologically acceptable acid addition salts, its quaternary ammonium salts, its oxides and its levorotatory and dextrorotatory isomers.

The compound of the invention of formula

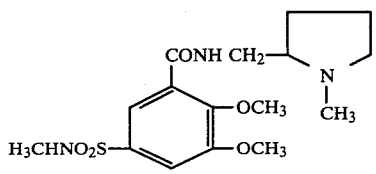

can be prepared by reacting a compound of formula

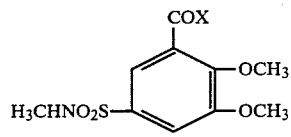

in which X stands for a halogen atom, a hydroxyl group or a group able to form a reactive acid derivative with 1-methyl-2-aminomethyl pyrrolidine or its reactive derivatives.

In the starting compound, the group able to form a reactive acid derivative is chosen from among the groups able to form lower alkyl esters such as methyl, ethyl, propyl, butyl, isobutyl, pentyl and isopentyl esters, reactive acid esters such as methoxymethyl esters, cyanomethyl esters, substituted or unsubstituted aromatic esters and N-hydroxyimide esters, acid azides, acid hydrazides, symmetrical anhydrides, mixed anhydrides such as, for example, those formed from carboxylic acid esters and haloformic esters, azolides such as triazolides, tetrazolides and in particular imidazolides, substituted ω-trihaloacetophenones, substituted α-oxobenzeneacetonitriles, nucleus-substituted benzamides or other equivalents or the compound of general formula:

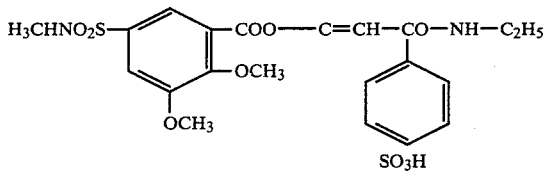

(formed from 2,3-dimethoxy-5-methylsulphamoyl benzoic acid and an isoxazolium salt). However, the invention is not limited to the reactive derivatives referred to hereinbefore.

According to the process of the invention, the amine can react in the form of a reactive derivative. For example, reference can be made to reaction products of the amine with phosphorus chlorides, phosphorus oxychloride, dialkyl or diaryl orthophenylene chlorophosphites, alkyl or aryl dichlorophosphites or 1-methyl-2-aminomethylpyrrolidine isothiocyanate or symmetrical or non-symmetrical N-(1-methyl-2-pyrrolidinylmethyl)-sulphamides or N,N'-bis-(1-methyl-2-pyrrolidinylmethyl)-urea or N-(1-methyl-2-pyrrolidinylmethyl)-enamine or any other equivalent.

The reactive derivatives referred to hereinbefore can react with the acid in situ or after preliminary isolation. However, the invention is not limited to the reactive derivatives described hereinbefore.

It is also possible to carry out the reaction of the free acid and the free amine in the presence of a condensing agent such as, for example, silicon tetrachloride, phosphoric anhydride or a carbodiimide such as dicyclohexylcarbodiimide or alkoxy acetylenes such as methoxy acetylene or ethoxy acetylene.

The amidification reaction can be carried out in the presence or absence of a solvent, optionally on ion exchanger resins.

The system used as solvents, which are inert with respect to the amidification reaction, are for example alcohols, polyols, benzene, toluene, dioxan, chloroform, diethyleneglycol, dimethyl ether. The solvent can also be in the form of an excess of the amine used as the starting substance. It may be preferable to heat the reaction mixture during amidification, e.g. up to the boiling point of the solvents referred to hereinbefore.

The compound obtained according to the process of the invention can, if necessary, react with pharmaceutically acceptable organic or mineral acids such as hydrochloric, hydrobromic, sulphuric, phosphoric, oxalic, acetic, tartaric, citric and methane-sulphonic acids in order to give acid addition salts.

If necessary, it may also react with alkyl halides or sulphates to give quaternary ammonium salts. It may also be oxidized by a per se known process, e.g. by means of hydrogen peroxide and manganese dioxide to give the N-oxide.

In order to illustrate the technical characteristics of the present invention, a number of examples will be described hereinafter, it being understood that these are not limitative either with respect to their performance or with respect to the applications thereof.

EXAMPLE 1

N-(1-methyl-2-pyrrolidinyl-methyl)-2,3-dimethoxy-5-methylsulphamoyl benzamide

Stage I: 2,3-dimethoxy-5-chlorosulphonyl benzoic acid 1620 cm³ of chlorosulphonic acid were placed in a round-bottomed flask equipped with a stirrer, a condenser and a thermometer, after which 164 g of 2,3-dimethoxybenzoic acid were added in portions, whilst maintaining the temperature at between 10° and 15° C.

After allowing the temperature to rise again, the mixture was stirred for 4 minutes at between 22° and 28° C. and was then maintained at ambient temperature.

The solution was then poured dropwise into a round-bottomed flask containing 600 g of crushed ice externally cooled so as to keep the temperature between 0° and 5° C. The precipitate formed was suction filtered, washed with water and dried with air.

207 g of 2,3-dimethoxy-5-chlorosulphonyl benzoic acid were obtained (melting point 155° to 156° C., yield 92%).

Stage II: 2,3-dimethoxy-5-methylsulphamoyl benzoic acid 200 g of a 33% aqueous methyl amine solution were placed in a round-bottomed flask equipped with a stirrer and a thermometer, after which 98.5 g of 2,3-dimethoxy-5-chlorosulphonyl benzoic acid were added in portions, whilst maintaining the temperature at between 0° and 5° C.

After allowing the temperature to rise again, the mixture was poured onto 1.7 liters of crushed ice. The solution was then filtered and treated with 130 cm$^3$ of concentrated hydrochloric acid. The crystals formed were suction filtered, washed with water and dried at 50° C.

83 g of 2,3-dimethoxy-5-methylsulphamoyl benzoic acid were obtained (melting point 164° to 165° C., yield 84%).

Stage III: methyl-2,3-dimethoxy-5-methylsulphamoyl benzoate 310 cm$^3$ of methyl alcohol were placed in a round-bottomed flask equipped with a condenser then, accompanied by cooling, 15.5 g of 93% sulphuric acid were poured in portionwise and finally 76 g of 2,3-dimethoxy-5-methylsulphamoyl benzoic acid were added.

After refluxing for 6 hours, the solution was cooled and poured into 3 liters of water containing 20 g of sodium carbonate. The crystals formed were suction filtered, washed with water and dried in air.

76 g of methyl-2,3-dimethoxy-5-methylsulphamoyl benzoate were obtained (melting point 76° C., yield 95%).

Stage IV: N-(1-methyl-2-pyrrolidinylmethyl)-2,3-dimethoxy-5-methylsulphamoyl benzamide 95 g of methyl-2,3-dimethoxy-5-methylsulphamoyl benzoate and 443 cm$^3$ of ethylene glycol were introduced into a round-bottomed flask equipped with a stirrer and a thermometer, accompanied by heating to 90° C.

The mixture was then cooled to 50° C., followed by the addition of 45 g of 1-methyl-2-aminomethyl pyrrolidine. The solution was stirred at 50° C. and kept at this temperature for a few hours. The solution was then taken up by 1.8 liters of water and acidified with 50 cm$^3$ of concentrated hydrochloric acid. The acid solution was filtered, then treated with 75 cm$^3$ of 20% ammonia. The crystals formed were suction filtered, washed with water and dried at 50° C.

After purification by passing through hydrochloride and recrystallisation of the base in isopropyl alcohol, 66 g of N-(1-methyl-2-pyrrolidinylmethyl)-2,3-dimethoxy-5-methylsulphamoyl benzamide were obtained (melting point 120° to 121° C., yield 54%).

EXAMPLE 2

Levorotatory N-(1-methyl-2-pyrrolidinylmethyl)-2,3-dimethoxy-5-methylsulphamoyl benzamide 170 g of methyl-2,3-dimethoxy-5-methyl-sulphamoyl benzoate and 850 cc of ethylene glycol were placed in a 2 liter round-bottomed flask.

The mixture was heated to 60° C. until completely dissolved and then cooled to 50° C. 80 g of levorotatory 1-methyl-2-aminomethyl pyrrolidine were added and the solution was kept at 50° C. until a sample was completely soluble in dilute acids.

The reaction mixture was then taken up with 3.5 liters of water. The crystals formed were suction filtered, washed with water and dried at 40° C. The 150 g of base obtained were dissolved in 500 cm$^3$ of absolute alcohol and then 155 cm$^3$ of a hydrochloric alcohol solution were added. The solution was heated and then filtered after adding vegetable black. After cooling, the hydrochloride precipitate was suction filtered, washed with absolute alcohol and dried at 50° C.

141 g of hydrochloride were obtained (melting point 156° to 158° C.). The 141 g of hydrochloride were then dissolved in 423 cm$^3$ of water. The solution obtained was filtered in the presence of vegetable black and then the base was precipitated by adding 35 cm$^3$ of 20% ammonia. The precipitate formed was suction filtered, washed with water and then dried at 50° C.

108.5 g of levorotatory N-(1-methyl-2-pyrrolidinylmethyl)-2,3-dimethoxy-5-methylsulphamoyl benzamide were obtained (melting point 111° to 112° C., yield 49.5%, $[\alpha]_D^{20} = -38°$ in a 5% dimethyl formamide solution).

EXAMPLE 3

Dextrorotatory N-(1-methyl-2-pyrrolidinylmethyl)-2,3-dimethoxy-5-methylsulphamoyl benzamide 170 g of methyl-2,3-dimethoxy-5-methylsulphamoyl benzoate and 850 cm$^3$ of ethylene glycol were placed in a 2 liter round-bottomed flask. The mixture was heated to 50° C. until dissolved and then 82 g of dextrorotatory 1-methyl-2-aminomethyl pyrrolidine were added. The solution was kept at 50° C. until a sample was completely soluble in dilute acids.

After cooling, the reaction mixture was taken up by 3.4 liters of water and 80 cm$^3$ of concentrated hydrochloric acid. The solution was filtered after adding vegetable black and then treated with 70 cm$^3$ of 20% ammonia. The precipitate formed after adding 300 g of potassium carbonate was suction filtered, washed with water and dried. The 180 g of base obtained were purified in accordance with the process of example 2.

133 g of dextrorotatory N-(1-methyl-2-pyrrolidinylmethyl)-2,3-dimethoxy-5-methylsulphamoyl benzamide were obtained (melting point 109° to 110° C., yield 61%, $[\alpha]_D^{20} = 38°.15'$ in a 5% dimethyl formamide solution.

EXAMPLE 4

N-(1-methyl-2-pyrrolidinylmethyl)-2,3-dimethoxy-5-methylsulphamoyl benzamide N-oxide 261 g of N-(1-methyl-2-pyrrolidinylmethyl)-2,3-dimethoxy-5-methylsulphamoyl benzamide and 875 cm$^3$ of absolute ethanol were placed in a 2 liter round-bottomed flask, followed by 142 cm$^3$ of 110 volumes hydrogen peroxide. The solution was heated at 45° C. for a few hours and then cooled to 40° C.

2 g of manganese dioxide were then added portionwise and the mixture was stirred for half an hour. After adding 20 g of vegetable black and filtration the filtrate was evaporated. The product obtained was recrystalized in water.

97 g of N-(1-methyl-2-pyrrolidinyylmethyl)-2,3-dimethoxy-5-methylsulphamoyl benzamide N-oxide were obtained (melting point 142° to 142° C., yield 35.5%).

The products according to the invention are used in the form of gelatin capsules, tablets, pastes, pills, granules and injectable solution, which are prepared in per se known manner. It is possible to use substances which are inert relative to the compounds of the invention such as lactose, magnesium stearate, starch, talc, cellulose, levilite, alkali metal lauryl sulphates, saccharose and vehicles conventionally used in medicinal preparations.

In order to prepare tablets, the chosen compound is mixed with starch and lactose by the process of successive dilutions. The mixture is granulated with methyl cellulose. Levilite, magnesium stearate and talc are added to the granular material before tableting is carried out.

It is possible to replace the methyl cellulose with any other appropriate granulating agent such as for example ethyl cellulose, polyvinyl pyrrolidone, starch paste, gum arabic, etc. The starch can also be replaced by a different disintegrating agent such as maize starch, carboxymethyl amylases, alginates, microcrystalline cellulose, etc.

To prepare injectable solution, it is possible to dissolve the compound according to the invention in the following acids: hydrochloric, levulinic, gluconic or glucoheptonic acids.

The solution prepared in sterile manner is made isotonic by an alkali metal chloride such as sodium chloride, after which preservatives are added.

It is also possible to prepare the same solution without adding preservatives, the ampule being filled under nitrogen and sterilised for 30 minutes at 100° C.

The compounds according to the invention can be administered at doses of 100 to 300 mg daily, the prepared daily dose being 150 mg. The following examples relate to pharmaceutical preparations obtained in conventional manner from the compounds of the invention.

EXAMPLE 5

Gelatin capsules

| | |
|---|---|
| N—(1-methyl-2-pyrrolidinylmethyl)-2,3-dimethoxy-5-methylsulphamoyl benzamide | 50 mg |
| dry potato starch | 30 mg |
| lactose | 113 mg |
| methyl cellulose 1500 | 1.6 mg |
| talc | 2.7 mg |
| magnesium stearate | 2.7 mg |
| for 1 capsule of | 200 mg |

EXAMPLE 6

Injectable solution

| | |
|---|---|
| N—(1-methyl-2-pyrrolidinylmethyl)-2,3-dimethoxy-5-methylsulphamoyl benzamide | 100 mg |
| N-hydrochloric acid | 0.27 mg |
| sodium chloride | 8 mg |
| water for injectable preparation | 2 ml |
| for 2 ml of solution | |

The compounds according to the invention have interesting pharmacological properties and are particularly active in the treatment of disorders of the lower urinary apparatus. Their low toxicity is compatible with use in human therapy without risk of side effects.

The acute toxicity of the compounds of the invention was determined on Swiss mice parenterally, (intravenously, intraperitoneally, subcutaneously) and orally.

Measurement of the lethal doses of N-(1-methyl-2-pyrrolidinylmethyl)-2,3-dimethoxy-5-methylsulphamoyl benzamide (compound) and its levorotatory isomer (compound 2) gave the following results:

| | TOXICITIES | | | |
|---|---|---|---|---|
| | $LD_{50}$ in mg/kg | | | |
| Compound | I.V. | S.C. | I.P. | P.O. |
| 1 | 130–135 | 936–960 | 315–323 | 992–1050 |
| 2 | 90–94.6 | 741–780 | 310–336 | 1080–1152 |

A pharmacological study of the compound of the invention which consisted of studying its action on the results of cystomanometry in the rabbit and rat was performed under the following conditions:

the animals were anesthesized with pentobarbitol and were given artificial respiration. The left outer jugular vein was catheterized to permit the I.V. injection of the studied product. The bladder was then exteriorized and the two ureters were connected and provided with two catheters, one of which was used to measure the intravesical pressure and the other for the vesical filling.

The vesical was filled by perfusion of 0.9% salt water at a constant flow rate of 40 ml/min for the rabbit and 5 ml/min for the rat.

The intravesical pressure before perfusion and the perfused water volume were measured.

The following parameters were studied:
the intravesical pressure before perfusion $P_1$
the intravesical pressure at the time of starting urination $P_2$
the $\Delta P = $ difference $P_2 - P_1$
the volume of salt water perfused
the quantity discharged during urination
the residual quantity only in the bladder.

The cystomanometry study was performed under the following conditions:
a first perfusion was carried out after stabilising the preparation for 5 minutes
a second perfusion was carried out 15 minutes after the first
a third perfusion was carried out 5 minutes after the second.

The study was performed by chronic and acute administration to the rabbit and acute administration to the rat.

The study of the rabbit was performed in the following manner:
10 male rabbits having an average weight of 2500±100 g were used as the control batch
for the chronic administration study, 10 male rabbits with an average weight of 2500±100 g were treated every morning for 8 days with N-(1-methyl-2-pyrrolidinylmethyl)-2,3-dimethoxy-5-methylsulphamoyl benzamide intramuscularly injected at a dosage of 10 mg/kg/day. The final injection was carried out 30 minutes before the experiment
for the acute administration study 2 batches of 10 male rabbits with an average weight of 2500±100 g were treated with N-(1-methyl-2-pyrrolidinylmethyl)-2,3-dimethoxy-5-methylsulphamoyl benzamide intravenously administered at doses of 5 and 50 mg/kg.

The acute administration study in the rat was carried out in the following manner:
10 male rats weighing on average 490±20 g were used as the control batch 20 male rats of average weight 480±20 g were treated with N-(1-methyl-2-pyrrolidinylmethyl)-2,3-dimethoxy-5-methylsulphamoyl benzamide administered intravenously at doses of 50 and 100 mg/kg.

For the controls and for all the treated batches the first perfusion is used as a standard for the following perfusions (each animal serving as its own control).

In the case of the acute administration of N-(1-methyl-2-pyrrolidinylmethyl)-2,3-dimethoxy-5-methylsulphamoyl benzamide to both the rabbit and the rat the product was injected at the end of the first perfusion.

There was a delay of 15 minutes before the two other perfusions (this was also respected for the controls in order to adhere to the same experimental conditions).

The following results were observed:

in the rabbit the intramuscular administration for 8 days of N-(1-methyl-2-pyrrolidinylmethyl)-2,3-dimethoxy-5-methylsulphamoyl benzamide at a rate of 10 mg/kg/day modifies the parameters in the following manner compared with the control batch reduction by about a third of the ΔP as from the first perfusion, the difference compared with the controls being reduced at the third perfusion considerable decrease of about half compared with the controls of the perfusion volume.

Variations in the same direction of the same parameters and in the same proportions are noted during the second and third perfusions after the acute I.V. administration of N-(1-methyl-2-pyrrolidinylmethyl)-2,3-dimethoxy-5-methylsulphamoyl benzamide at doses of 5 and 50 mg/kg. The differences compared with the controls are highly significant and on the basis thereof it is concluded that N-(1-methyl-2-pyrrolidinylmethyl)-2,3-dimethoxy-5-methylsulphamoyl benzamide lowers the urinary threshold in the anesthetized rabbit.

In the rat:

The same phenomena as in the rabbit are not observed.

However, there is a significant increase in the urinary volume during the second and third perfusions, particularly at an I.V. dosage of 50 mg/kg.

These results in the animal show a modified vesical behaviour which varies with species and have led to an investigation of the action on the urination in man.

The gaseous cystomanometric study in man revealed an increase in the vesical tolerance in two cases of serious neurological bladder.

A 34 year old man suffering from multiple sclerosis suffered from incontinence, pollakisuria and the very frequent need to urinate. The intramuscular injection of two 100 mg ampules of the compound of the invention delayed the need to urinate for a volume of 150 cm$^3$, compared with 80 cm$^3$ before treatment.

A 58 year old women having psychogenic urinary disorders with incontinence and pollakisuria received two 100 mg ampules of the compound according to the invention by the intramuscular route. She only needed to urinate for a volume of 400 cm$^3$; compared with 200 cm$^3$ before treatment. She was able to voluntarily prevent urination for 2 minutes compared with 15 seconds before treatment.

1. OPEN STUDIES

These studies related to more than 200 patients and led to the retention of two indications:

functional disorders of the lower urinary apparatus of men and particularly in the case of prostatism cystalgias with clear urine in women.

2. To check these impressions, two studies were carried out according to the double blind procedure:

(a) In females

Due to the absence of a reference product the activity of the present product was compared with a placebo. The superiority of N-(1-methyl-2-pyrrolidinylmethyl)-2,3-dimethoxy-5-methylsulphamoyl benzamides is very significant $p < 0.001$.

(b) In males

The study was carried out in comparison with the only possible reference product: lipidosterolic complex extracted from pygeum africanum. Here again, the superiority of the product is statistically significant $p < 0.05$.

For both the above indications, the ease of oral treatment was appreciated and the tolerance was excellent.

The product was also found to be remarkably active by the intramuscular or intravenous routes in the treatment of pelvic spasms on probe after urological or gynecological surgery.

We claim:

1. A compound selected from the group consisting of N-(1-methyl-2-pyrrolidinylmethyl)-2,3-dimethoxy-5-methylsulphamoyl benzamide, its N-oxide, its pharmacologically acceptable acid addition salts, its quaternary ammonium salts and levorotatory and dextrorotatory isomers thereof.

* * * * *